(12) United States Patent
Chiari (10) Patent No.: US 10,077,379 B2
(45) Date of Patent: Sep. 18, 2018

(54) SILANE COPOLYMERS AND USES THEREOF

(76) Inventor: Marcella Chiari, Milan (IT)

( * ) Notice: Subject to any disclaimer, the term of this patent is extended or adjusted under 35 U.S.C. 154(b) by 560 days.

(21) Appl. No.: 13/639,605

(22) PCT Filed: Apr. 8, 2011

(86) PCT No.: PCT/EP2011/055574
§ 371 (c)(1),
(2), (4) Date: Jan. 22, 2013

(87) PCT Pub. No.: WO2011/124715
PCT Pub. Date: Oct. 13, 2011

(65) Prior Publication Data
US 2013/0115382 A1 May 9, 2013

Related U.S. Application Data

(60) Provisional application No. 61/322,453, filed on Apr. 9, 2010.

(51) Int. Cl.
| | | |
|---|---|---|
| *C09D 179/08* | (2006.01) | |
| *B01L 3/00* | (2006.01) | |
| *C08F 220/56* | (2006.01) | |
| *C08F 224/00* | (2006.01) | |
| *C08F 230/08* | (2006.01) | |

(Continued)

(52) U.S. Cl.
CPC .......... *C09D 179/08* (2013.01); *B01L 3/5027* (2013.01); *B01L 3/502707* (2013.01); *C08F 220/56* (2013.01); *C08F 224/00* (2013.01); *C08F 230/08* (2013.01); *C09D 133/26* (2013.01); *C09D 137/00* (2013.01); *C09D 143/04* (2013.01); *C09D 163/10* (2013.01);
(Continued)

(58) Field of Classification Search
CPC ............ A01K 2217/05; A01K 61/0336; A61K 38/00; C07K 14/43545; C07K 14/4705
See application file for complete search history.

(56) References Cited

U.S. PATENT DOCUMENTS

| | | | | |
|---|---|---|---|---|
| 5,723,344 | A | * | 3/1998 | Mabilat ............ G01N 33/54353 422/566 |
| 6,410,668 | B1 | | 6/2002 | Chiari |
| 2006/0141464 | A1 | * | 6/2006 | Chiari ................... C08F 220/56 435/6.19 |

FOREIGN PATENT DOCUMENTS

EP       1567569 B1       7/2008

OTHER PUBLICATIONS

Marina Cretich, Valentina Sedini, Francesco Damin, Gabriele Di Carlo, Claudio Oldani and Marcella Chiari. Functionalization of poly(dimethylsiloxane) by chemisorption of copolymers: DNA microarrays for pathogen detection. Jan. 31, 2008. Sensors and Actuators B. vol. 132. pp. 258-264.*

(Continued)

*Primary Examiner* — Dah-Wei D. Yuan
*Assistant Examiner* — Kristen A Dagenais
(74) *Attorney, Agent, or Firm* — The Marbury Law Group, PLLC (57) ABSTRACT

The invention relates to a method to reduce the electroosmotic flow in a capillary or in a channel and to a method to reduce the attachment of biological species to a surface comprising the step of coating said capillary, channel or surface with a copolymer comprising a surface interacting monomer, a monomer bearing a chemically active group and an ethylenically unsaturated silane monomer.

8 Claims, 9 Drawing Sheets

(51) Int. Cl.
  *C09D 133/26*  (2006.01)
  *C09D 137/00*  (2006.01)
  *C09D 143/04*  (2006.01)
  *G01N 27/447*  (2006.01)
  *C09D 163/10*  (2006.01)

(52) U.S. Cl.
  CPC .. *G01N 27/44704* (2013.01); *B01L 3/502753* (2013.01)

(56) References Cited

OTHER PUBLICATIONS

Marina Cretich, Valentina Sedini, Francesco Damin, Gabriele Di Carlo, Claudio Oldani and Marcella Chiari. Functionalization ofpoly(dimethylsiloxane) by chemisorption of copolymers: DNA microarrays for pathogen detection. Jan. 31, 2008. Sensors and Actuators B. vol. 132. pp. 258-264.*
Marcella Chiari, Marina Cretich, Francesco Damin, Gabriele Di Carlo, and Claudio Oldani. Advanced polymers for molecular recognition and sensing at the interface. Jan. 16, 2008. Journal of Chromatography B. vol. 2008. 89-103.*
Marina Cretich, Valentina Sedini, Francesco Damin, Gabriele Di Carlo, Claudio Oldani and Marcella Chiari. Functionalization of poly(dimethylsiloxane) by chemisorption of copolymers: DNA microarrays for pathogen detection. Jan. 31, 2008. Sensors and Actuators B. vol. 132. pp. 258-264. (Year: 2008).*
Marcella Chiari, Marina Cretich, Francesco Damin, Gabriele Di Carlo, and Claudio Oldani. Advanced polymers for molecular recognition and sensing at the interface. Jan 16, 2008. Journal of Chromatography B. vol. 2008. 89-103. (Year: 2008).*
Marina Cretich, Marcella Chiari, Giovanna Pirri, and Alessandro Crippa. Electroosmotic flow suppression in capillary electrophoresis : Chemisoption of trinnethoxy silane-modified polydimethylacrylatemide. 2005. Electrophoresis. vol. 26. pp. 1913-1919 (Year: 2005).*
International Search Report issued in corresponding PCT Application No. PCT/EP2011/055574, dated May 23, 2011.
International Preliminary Report on Patentability issued in corresponding PCT Application No. PCT/EP2011/055574, dated Oct. 18, 2012.
Chiari M et al: "Advanced polymers for molecular recognition and sensing at the interface", Journal of Chromatography B: Biomedical Sciences & Applications, Elseveier, Amsterdam, NL, vol. 8661-26,28,32,33, No. 1-2, Apr. 14, 2008, pp. 89-103.
Cretich M et al; "Functionalization fo poly(dimethylsiloxana) by chemisorption of copolymers: DNA michoarrays for pathogen detection", Sensors and Actuators B, Elsevier Sequoia S.A., Lausanne, CH, vol. 132, No. 1, May 28, 2008, pp. 258-264.
Pirri G., et al., "Characterization of a polymeric adsorbed coating for D NA microarray glass slides" Anal. Chem., 2004, 76, 1352-8.
Cretich M., et al., "High sensitivity protein assays on microarray silicon slides" Anal. Chem., 2009, 81, 5197-5203.
Cretich M., et al., "Electroosmotic flow suppression in capillary electrophoresis: chemisorptions of trimethoxy silane-modified polydimethylacrylamide" Electrophoresis, 2005, 26, 1913.
Wang J, "From DNA biosensors to gene chips" Nucleic Acids Research, 2000, vol. 28, No. 16 3011-3016.
Leca-Bouvier, B., et al., "Biosensors for protein detection: a review" Analytical Letters, vol. 38, Issue 10 2005, pp. 1491-1517.

* cited by examiner

-Spotting
-Scanning with ScanArray Lite (Perking Helmer); laser power: 30%; photomultiplier gain: 60%
-washing

SILANE COPOLYMERS AND USES THEREOF

CROSS-REFERENCE TO RELATED APPLICATIONS

This application is a National Stage application of PCT International Application Serial No. PCT/EP2011/055574, filed Apr. 8, 2011, which claims priority from U.S. Provisional Application No. 61/322,453, filed Apr. 9, 2010.

FIELD OF THE INVENTION

The invention relates to synthetic random copolymers obtained by radical polymerization. Such polymers may be used as coating agents.

BACKGROUND OF THE INVENTION

Thin coatings applied to the surface of materials can improve the properties of objects dramatically as they allow control of the interaction of a material with its environment. Examples of interface properties which can be controlled by deposition of a thin organic film onto a surface include friction, adhesion, adsorption of molecules from the surrounding environment, or wetting with water or other liquids, control of electroosmotic flow (EOF) in micro-channel and nano-channels.

In the scientific and patent literature there are examples of film formation that occur either by physisorption or by chemisorption. The synergic combination of the two mechanisms was introduced by the patent EP1567569, and by the U.S. application Ser. No. 10/536,306. In these two documents the use of a copolymer made of three distinct components, each with a specific function, was disclosed: i) a monomer that promotes surface adsorption, ii) a monomer that promotes the covalent binding with biomolecules such as DNA and proteins and iii) a third monomer that stabilizes the adsorbed film by covalently reacting with functional groups present on the surface. The use of the copolymer reported in EP1567569, and by the U.S. application Ser. No. 10/536,306 is limited to the production of a coating for the attachment of biological molecules to different surfaces.

The use of poly(dimethylacrylamide)-based copolymers bearing functionalities reactive towards nucleophiles to coat various materials was introduced by the above mentioned patents. The film formed on the surface confers to the support underneath the ability to immobilize bioactive species. The above cited documents disclose the use of a copolymer made of two or more monomers playing different roles. In particular, the polymer backbone (the monomer constituent present in larger amount) promotes polymer physisorption whereas the other functional monomers are chemically reactive with either the material of the surface or biological molecules.

The above mentioned EP patent describes a method to immobilize biological molecules to a glass surface based on the use of copolymers with a long segment of poly(dimethylacrylamide) functionalized either by random incorporation of N-acryloyloxysuccinimide or glycidyl methacrylate comonomers, optionally also incorporating an allyl monomer able to react with surface silanols. Furthermore, Pirri G., et al. (Characterization of a polymeric adsorbed coating for DNA microarray glass slides, *Anal Chem.*, 2004, 76, 1352-8) have suggested that the third monomer could be a silane monomer.

The copoly(dimethylacrylamide-acryolyloxysuccinmide methacryloylpropyltrimethoxysilane)-copoly(DMA-MAPSA-NAS) has been extensively used to attach biological molecules on several materials (Cretich M., et al., High Sensitivity Protein Assays on Microarray Silicon Slides, *Anal. Chem.*, 2009, 81, 5197-5203, Cretich M. et al., Functionalization of poly(dimethylsiloxane) by chemisorption of copolymers: DNA microarrays for pathogen detection, Sens. and Actuat. B-Chem., 2008, 132, 258-264.).

The copolymer previously reported in EP1567569 and in the publications cited above promotes the attachment of biomolecules by exposing functional active esters that are available for reaction with the nucleophiles groups on the protein, peptide or amino-modified DNA. The active ester on the monomer plays, at the same time, the role of stabilizing the coating by a covalent binding with the surface and grafting the bioactive species by reacting with their exposed functionalities. In the above cited paper by Pirri et al. (*Anal Chem.*, 2004, 76, 1352-8) it has been demonstrated that the introduction of a third silane monomer constituent is highly effective in stabilizing the binding of the polymer with the surface.

Polymer for Suppression or Control of Electroosmotic Flow

In most capillary electrophoresis (CE) applications it is necessary to suppress or control electroosmotic flow in order to exploit the potentiality of the technique. In some cases, for instance at high pH, the EOF may be too rapid resulting in the elution of the analytes before separation has occurred. In addition, the negatively charged wall can cause adsorption of cationic solutes through coulombic interactions. An effective modification of surface properties can be achieved by coating the wall with a polymer. Neutral polymers physi- or chemi-sorbed on the capillary wall, strongly decrease EOF by shielding surface charge and by increasing local viscosity. Silica surfaces, exposed to very diluted solutions of certain polymers, develop dense polymer layers which involve hydrogen bonding, monopolar, dipolar or hydrophobic forces. In the past, the author has described polymer coatings with characteristics of irreversibility obtained by adsorption of copolymers of dimethylacrylamide and allylglycidyl ether (U.S. Pat. No. 6,410,668). Polymer-surface, solvent-surface, and polymer-solvent interactions were optimized to increase the stability of the coating. In particular, the molecular weight was found to strongly impact layer stability as the sticking energies per chain increase in proportion to the number of monomer units.

One of the problems of CE, is that the coating is challenged by a number of factors including shear forces, competition by various species present in the running buffer (urea, detergents proteins). Therefore, the strongest and most enduring interfaces possible are preferred.

The publication Cretich M. et al., (Electroosmotic flow suppression in capillary electrophoresis: chemisorption of trimethoxy silane-modified polydimethylacrylamide, *Electrophoresis*, 2005, 26, 1913) discloses strategies to form irreversible polymer films on a capillary wall that involve polymer physisorption followed by its covalent attachment to the surface.

Two polymers were independently disclosed by the U.S. Pat. No. 6,410,668 and by the Chiari et al., publication (*Electrophoresis*, 2005, 26, 1913) reported above. In both polymers, dimethylacylamide is present as the surface interacting monomer but they differ from the polymers disclosed in the present invention. The polymer of U.S. Pat. No. 6,410,668 lacks of the silane condensable monomer whereas the polymer of the publication lacks of the chemically active monomer (epoxy group). It was found that the polymer of the U.S. Pat. No. 6,410,668 requires a high molecular weight to form a stable coating whereas the polymer of the publication lacks of robustness, often failing to provide the desired performance.

Adsorpion of Biomoleucles

The adsorption of biomolecules through specific and nonspecific interactions is important in industrial, medical, and diagnostic applications.

An example of the importance of controlling protein adsorption is given by the biosensors that are routinely and increasingly used. In biosensors, specific interactions between biomolecules, such as complementary DNA strands (Joseph Wang, From DNA biosensors to gene chips, Nucleic Acids Research, 2000, Vol. 28, No. 16 3011-3016) or antibody-antigen pairs (B. Leca-Bouvier and L. J. Blum, Biosensors for Protein Detection: A Review, Analytical Letters, Volume 38, Issue 10 2005, pages 1491-1517) are necessary. The accuracy and reliability of these molecular diagnostic devices are currently hampered by their lack of sensitivity due to a low signal-to-noise ratio. A factor that plays a major role in reducing assay sensitivity is the nonspecific adsorption of biomolecules. The tendency of proteins to adsorb non-specifically to most solid surfaces is responsible for this phenomenon. A protein molecule has various hydrophobic or charged domains that can bind strongly with hydrophobic or oppositely charged surfaces. The hydrophobic interaction is particularly prevalent and is the dominant reason for fouling of a surface.

To solve the problems of non specific adsorption of bioactive species, considerable basic and applied researches have been devoted to the surface modification of various materials. A variety of "antifouling" layers have been employed to reduce the amount of nonspecifically adsorbed molecules on surfaces. Poly(ethylene glycol) (PEG), polysaccharides and polyionic layers have all been successfully incorporated as effective antifouling layers. Generally, there are two ways to achieve the surface modification of materials with polymers: physisorption and covalent attachment. Modification through physisorption of a polymer is technologically simpler, in particular, when the film is produce by dip coating. The disadvantage of physisorbed coatings is their stability which is controlled by the hydrodynamic size of the adsorbing chains. In poly-disperse systems, short chains adsorb more rapidly than long ones but long chains are preferred on the surface at equilibrium. This leads to an exchange between long and short chains at intermediate stages of adsorption. In a radical polymerization it may be difficult to control polymer molecular weight and polydispersity. This lack of reproducibility on the composition of the polymer chains can translate into a poor reproducibility of some coating characteristics such as long term stability, thickness and swelling behavior. In addition, physisorption is an equilibrium process and desorption can occur under certain circumstances.

In an effort to overcome the problems of coating instability, a new family of polymer-silane, that rapidly adsorb on the wall from ultra-diluted aqueous solutions, was synthesized and used to form a coating on capillary and microfluidic devices. Upon thermal treatment, silyl groups, pending from the backbone, condensate with surface silanols and covalently bind the copolymer to the surface. The results of the investigation on the characteristics of the coating formed by this polymer proves that, by a combination of physisorption and chemisorption, it is possible to dramatically increase coating adhesion strength leading to coatings of longer lifetime In the present invention, it was surprisingly found that the combination of three specific ingredients in a linear polymer leads to formation of coating with improved performance as the specific polymer composition allows increasing the number of surface anchoring points. For instance, when use in capillary or micro-channel electrophoresis to suppress EOF, poly(dimethylacrylamide) containing silane and glycidyl methacrylate monomers is more strongly attached to the surface making the coating more robust, reproducible and highly performing to suppress EOF. A similar effect could not be obtained by increasing the concentration of the two individual silane and glycidyl methacrylate monomers. In fact, by increasing the silane molar fraction, the polymer becomes too prone to condensation and electrically charged whereas, by increasing the content of epoxy groups, the surface becomes reactive towards biomolecules that are separated in the capillary leading to band broadening and dramatic decrease of the separation performance. Only the synergistic presence of the two monomers, the silane and the epoxy, allows formation of a coating that combines the advantages of low polymer molecular weight and high coating stability. Stable coatings are generated by covalent attachment of polymers to surfaces but they need cumbersome and multistep chemical reactions which may be difficult to control.

The polymer of the invention overcomes problems such as irreproducibility and instability of physisorbed coating. They are particularly advantageous because due to a combination of physic- and chemi-sorption mechanisms, the polymers of the invention can i) suppress/control electroosmotic flow in electrophoresis ii) minimize non specific adsorption of proteins onto coated surfaces and iii) increase hydrophilicity of the surface on which they are applied.

DESCRIPTION OF THE INVENTION

This invention discloses a family of polymers and their use in the formation of a film on a wide variety of materials through a process that conjugates physi-sorpion and chemi-sorption.

The present invention identifies the right monomer combination and content. This combination dramatically increases the coating adhesion strength leading to films that are stable in harsh condition of use. The present invention discloses polymer compositions and methods to use these polymers to make a coating for i) suppression of electroosomtic flow in micro-nano-channels electrophoresis, ii) prevention of non specific adhesion of biological molecules and iii) to increase hydrophilicity of the surface on which they are applied.

In the present invention it is disclosed a polymer composed of a) a first surface interacting monomer, b) a second monomer bearing a chemically active group and a c) a third ethylenically unsaturated silane monomer.

The present invention discloses also the use of the above polymer to form an irreversible coating on various surfaces in three novel related applications such as suppression of EOF, suppression of biomolecule surface interaction, increasing surface wettability with water. The polymer may be used to obtain i) suppression of electroosmotic flow in microchip/microchannel electrophoresis, ii) suppression of unwanted interactions between the surface and the biological species and iii) increasing surface hydrophilicity.

In synthesis, the present invention sets the characteristics of a class of polymers that form a coating on a variety of materials. The copolymer must contain i) segments that interact with the surface by weak, non covalent interactions such as hydrogen bonding, Van der Waals or hydrophobic forces (polymer backbone), ii) pending silane hydrolysable monomers that promote condensation of the polymer with surface silanols (when presents) or between different chains and iii) chemically active monomers whose reactivity is selected on the basis of the function of the surface film and of the characteristics of the material on which the coating is made. The chemical reactive groups can either be introduced by copolymerization of monomer or oligomers or by subsequent modification of polymer pendant functionalities.

The optimal polymer composition comprises: a) a first surface interacting monomer, b) a second monomer bearing a chemically active group and a c) third an ethylenically unsaturated silane monomer. This composition is particularly suitable to form an irreversible coating on various surfaces.

The terpolymer in which the surface interacting monomer is dimethylacrylamide, the monomer bearing a chemically active group is glycidyl methacrylate (GMA) and the ethylenically unsaturated silane monomer is gamma-(meth)-acryloxypropyltrimethoxy silane provided the best results in terms of EOF suppression leading to formation of coating on fused silica capillaries that reduce EOF to a value lower than $2.10^{-9}$ cm$^2$/Vs. This polymer forms a coating that suppresses EOF and protein surface interaction even if it contains epoxy functionalities that are reactive towards proteins. The antifouling behavior might result from the orientation of the epoxy groups on the surface. If the content of epoxy in the polymer is properly adjusted these groups are not available for binding, by covalent reaction, specific nucleophilic groups on the biomolecules, thus contributing only to the stabilization of the polymer film on the surface.

In the present invention, new copolymer formulations that form films that, besides suppressing EOF, prevent adhesion of biological species on the surface of any material on which the film can be formed are disclosed.

The invention resides in the use of a polymeric backbone made of a polymer that establishes surface interaction, the insertion on the polymer of groups that depending on the nature of the substrate can form covalent bonds with chemical groups on the surface and third the presence of a condensable silane group that stabilizes the film either by condensing silanols on contiguous chains or on the surface.

Depending on the characteristics of the polymer for instance if the chemically reactive groups are well exposed on the surface and prone to react with chemical groups on the biomolecules, it might be necessary to introduce a further step of blocking after coating formation. The blocking is aimed at blocking the functional groups on the surface and may be carried out by reacting the coated surface with a molecule bearing an appropriate functional group. An example is a ter polymer in which the surface interacting monomer is dimethylacrylamide (DMA), the monomer bearing a chemically active group is N-acryloyloxysuccinimide (NAS) and the ethylenically unsaturated silane monomer is gamma-methacryloxypropyltrimethoxy silane (MAPS). The use of this polymer to form a coating that binds biomolecules to surfaces was introduced by Chiari's group (Pirri et al., *Anal Chem.*, 2004, 76, 1352-8). The use this polymer as a coating for the suppression of protein surface interactions is not disclosed. In order to use this polymer as a coating for the suppression of protein surface interactions it may be necessary to block, through a specific reaction, the chemically reactive groups that remain on the surface after formation of the coating. The binding capacity of the dimethylacrylamide, N-acryloyloxysuccinimide (NAS) and gamma-methacryloxypropyltrimethoxy silane ter-polymer are fully suppressed by reacting the active ester of the polymer with the primary-amino of the hydroxyl aminoethanol. Upon deactivation of the active esters, the surface becomes extremely resistant to non-specific adsorption of bioactive species. This polymer forms a coating on fused silica capillaries reducing EOF to a value lower than $2.10^{-8}$ cm$^2$/Vs. This value of EOF is not negligible and might result from the presence of charges on the polymer chains that coat the inner capillary wall due to spontaneous hydrolysis of N-acryloyloxysuccinimide. However, a reduced flow combined with a reduced protein surface interaction is advantageous either in capillary or micro/nano-channel electrophoresis.

The reaction between the surface immobilized functional groups (for instance NAS) with reactive moieties in solution (for instance ethanolamine or aminomethoxypolyethyleneglycol 2,000, or aminopolyethyleneglycol or aminomethoxypolyethyleneglycol of other sizes such as aminoPEG 5000 and 10000) can be exploited to block surface reactive functionalities which, upon hydrolysis might generate surface charges that cause electroosmotic flow. The blocking reaction can also be used to improve surface resistance to protein or ssDNA interaction.

It is therefore the object of the present invention a method to reduce the electroosmotic flow in a capillary or in a channel comprising the steps of:
  coating said capillary or channel with a copolymer comprising:
  i) a surface interacting monomer,
  ii) a monomer bearing a chemically active group and
  iii) an ethylenically unsaturated silane monomer;
  optionally washing the capillary or channel with water and/or solvent;
  optionally drying the capillary or channel;
  optionally exposing the capillary or channel to a chemical entity able to block residual functional groups of the copolymer.

It is a further object of the present invention a method to reduce the attachment of biological species to a surface comprising the steps of:
  coating said surface with a copolymer comprising:
  i) a surface interacting monomer,
  ii) a monomer bearing a chemically active group and
  iii) an ethylenically unsaturated silane monomer;
  optionally washing the surface with water and/or solvent;
  optionally drying the surface;
  optionally exposing the surface to a chemical entity able to block surface reactive functionalities of the copolymer.

Preferably the surface interacting monomer of the copolymer is selected from the group of acrylamide, methacrylamide each being independently mono- or di-substituted on the nitrogen by C1 to C12 linear or branched alkyl, halo-substituted C1 to C12 alkyl, methoxy-substituted C1 to C12 alkyl or hydroxyl-substituted C1 to C12 alkyl, or vinylpyrrolidone.

Preferably the surface interacting monomer is dimethylacrylamide or diethylacrylamide. In a preferred embodiment the % by weight of the surface interacting monomer varies from 10% to 98%, preferably it varies from 75 to 98%, still preferably it varies from 90 to 98%.

In a preferred embodiment the chemically active group of the monomer bearing a chemically active group is selected from the group of: thiols, primary amines, secondary amines, tertiary amines, quaternary ammoniums, phosphines, alcohols, carboxylic acids, vinylsulfonyls, aldehydes, epoxides, hydrazides, succinimidyl esters, carbodiimides, maleimides, iodoacetyls, isocyanates, isothiocyanates, aziridines, sulfonates or halides.

Preferably the monomer bearing a chemically active group is a methacrylate or a succinimide.

Still preferably the monomer bearing a chemically active group is glycidyl methacrylate or N-acryloyloxysuccinimide.

In a preferred embodiment the % by weight of the monomer bearing a chemically group varies from 1% to 75%, preferably it varies from 1% to 5%, still preferably it varies from 2% to 4%.

In a preferred embodiment the ethylenically unsaturated silane monomer of the copolymer is selected from the group of: an alkoxy silane monomer, an acyloxy silane monomer or a mixture thereof.

Preferably the ethylenically unsaturated silane monomer of the copolymer is represented by the formula:

wherein R is an ethylenically unsaturated hydrocarbyl, hydrocarbyloxy or (meth)acryloxyhydrocarbyl group, R' is an aliphatic saturated hydrocarbyl group, n is 0 or 1 or 2 and Y is a hydrolysable organic group.

Still preferably R is vinyl, allyl, isopropenyl, butenyl, cyclohexenyl or gamma-(meth)acryloxypropyl.

Yet preferably Y is methoxy, ethoxy, formyloxy, acetoxy, propionyloxy.

In a preferred embodiment the ethylenically unsaturated silane is selected from the group of: vinyltrimethoxy silane, vinylbismethoxyethoxy silane, vinyltriethoxy silane, gamma-(meth)acryloxypropyltrimethoxy silane, gamma-(meth)-acryloxypropyltriethoxy silane and vinyltriacetoxy silane.

Preferably the ethylenically unsaturated silane monomer is gamma-(meth)-acryloxypropyltrimethoxy silane.

Still preferably the % by weight of the ethylenically unsaturated silane monomer varies between 0.001% and 15%, preferably it varies between 0.01% and 15%, yet preferably It varies between 0.1% and 3%.

In a preferred embodiment the copolymer comprises dimethylacrylamide, glycidyl methacrylate and gamma-(meth)-acryloxypropyltrimethoxy silane.

Preferably dimethylacrylamide is present in an amount of 95% by weight, glycidyl methacrylate is present in an amount of 4% by weight and gamma-(meth)-acryloxypropyltriethoxy silane is present in an amount of 1% by weight.

Preferably the copolymer comprises dimethylacrylamide, N-acryolyloxysuccinmide and is gamma-(meth)-acryloxypropyltrimethoxy silane.

Still preferably dimethylacrylamide is present in an amount of 97% by weight, N-acryolyloxysuccinmide is present in an amount of 2% by weight and gamma-(meth)-acryloxypropyltrimethoxy silane is present in an amount of 1% by weight.

In a preferred embodiment the blocking is performed by an agent selected from: ethanolamine, aminomodified polyethylenglycol, peptides, peptoids or synthetic polymers.

In a preferred embodiment the capillary or channel or surface is pre-activated by a washing step with NaOH and/or acidic solutions or by plasma treatment.

It is a further object of the invention a copolymer comprising:
  i) a surface interacting monomer as defined above,
  ii) an oxyrane and
  iii) an ethylenically unsaturated silane monomer as defined above.

Preferably the copolymer comprises dimethylacrylamide, glycidyl methacrylate and gamma-(meth)-acryloxypropyltriethoxy silane.

It is a further object of the invention the use of the copolymers comprising:
  i) a surface interacting monomer as defined above,
  ii) an oxyrane and
  iii) an ethylenically unsaturated silane monomer as defined above as a coating agent.

It is a further object of the invention a capillary or a channel with a reduced electroosmotic flow obtained by the method of the invention.

It is a further object of the invention a surface with a reduced attachment of biological species flow obtained by the method of the invention.

In the present invention, preferably the channels have a diameter in the micrometer range. As an example in the methods defined above, the coating may be carried out by flowing aqueous solution of the copolymer of the invention into the capillary or channel. Preferably the copolymer is dissolved at 2% w/v in aqueous solution of ammonium sulphate at 20% of its saturation concentration.

The coating on the surface, which may be a solid support may occur by contacting the surface with a solution of the copolymer in an organic solvent.

In the methods above the drying step may be performed at a temperature from room temperature to 100° C., preferably 80° C.

In the present invention, polymers that are soluble in water are used to form a coating, preferably by dip coating in 2% w/v polymer dissolved in water or in an aqueous solution of ammonium sulphate at 20% of its saturation concentration. Polymers that are soluble in organic solvent form a coating by contacting the surface to be coated with solutions of the polymer in different types of organic solvents (THF, DMF) in a concentration range from 1 to 10%.

In the present invention, materials on which the coating is made: may be glass, silicon, silicon oxide, nitride, polydimethylsiloxane, plastic, Teflon, polystyrene, gold, indium thin oxide, just to mention some of the possible materials. The material can be in any shape: flat substrates, tubes, capillaries, nanopore walls, wells, non sensor areas of all possible geometry and more specifically biosensors.

In the present invention, biological species include: enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix material and/or its individual components, pharmaceuticals, and therapeutics, for example. Cells, such as, mammalian cells, reptilian cells, amphibian cells, avian cells, insect cells, planktonic cells, cells from non-mammalian marine vertebrates and invertebrates, plant cells, microbial cells, protists, genetically engineered cells, and organelles, such as mitochondria, are also bioactive species. In addition, non-cellular biological entities, such as viruses, virenos, and prions are considered bioactive species. The term "adsorption" is defined as a reversible chemical combination due to any of the weaker classes of chemical bonding forces. Examples of particle association include hydrogen bonding, electrostatic attraction, London forces, van der Waals forces, and hydrophobic interactions The following, non-limiting, examples illustrate how the polymers of the invention are used in EOF and protein/surface interaction suppression in capillary electrophoresis and microarray experiments. They are not intended to limit in any way the field of the inventions.

EXAMPLES

Example 1: Synthesis of copoly(dimethylacrylamide-co-N-acryloyloxysuccinimide-co-methacryloxypropyltrimethoxy silane)-Copoly(DMA-NAS-MAPS)

Dimethylacrylamide (molar fraction 97%) (Aldrich), N-acryloyloxysuccinimide (molar fraction 2%) (Sigma) and methacryloxypropyltrimethoxy silane (Aldrich)(molar fraction 1%) were dissolved at 10% w/v total concentration, in dried tetrahydrofuran (THF) (Sigma) in a round-bottomed flask, equipped with condenser, magnetic stirring and nitrogen connection. The solution was degassed by alternating a nitrogen purge with a vacuum connection, over a 30 min period. Azobisisobutyronitrile (13 mg) (AIBN) (Fluka) was added to the solution which was then warmed to 65° C., and was maintained at this temperature under a slightly positive pressure of nitrogen for 24 hours. After the polymerization was completed, the polymer was precipitated by pouring the solution in petroleum ether (ratio THF/petroleum ether 1:10). The polymer was dried under vacuum for 2 h at 80° C.

The polymer was dried under vacuum for 2 h at room temperature and stored in a dry atmosphere at −20° C.

13C-NMR (DMSO), δ (ppm): 174.6 (backbone carbonyl), 166 (succinimide carbonyl) 40-30 (metylene carbons). The degree of succinimide insertion was determined from the ratio of the integrals of backbone and succinimide carbons and the NAS molar fraction was found to be 0.015.

The GPC scheme consists of four Shodex aqueous GPC columns in series: OHpak SB-G (guard column), OHpak SB-806M HQ, OHpak SB-804 HQ, and OHpak SB-802.5 HQ. Each column is packed with a polyhydroxymethacrylate gel and decreases in exclusion limit. The columns were maintained at 25° C. using an Agilent 1200 thermostatted column compartment.

A MALS detector consisting of a DAWN HELEOS II instrument (Wyatt Technology), which detects scattered light at 18 angles. The DAWN HELEOS II measures the radius as well as the absolute molecular weight of the polymer in solution. The MALLS instrument is in-line with an Optilab rEX (Wyatt Technology) refractive index detector. The Optilab rEX measures the dn/dc value of the polymer in solution. The polymer sample was diluted to a concentration of 1 mg/ml using the GPC mobile phase (GPC buffer: 100 mM NaCl, 50 mM NaH2PO4, and 200 ppm NaN3). The flow rate through the GPC-MALLS system was held at a constant 0.3 mL/min. The sample was run three times through the GPC-MALLS to test for reproducibility. Each run injected 100 µL of sample to be analyzed. The Mn was 1.483E+04 (g/Mol), the Mw3.620E+04 (g/Mol), the polydispersity 2.443 (Mn/Mw), the gyration radius was 10.07 nm.

Example 2: Synthesis of copoly(dimethylacrylamide-co-glycidyl methacrylate-co-methacryloxypropyltrimethoxy silane)-Copoly(DMA-GMA-MAPS)

Dimethylacrylamide (molar fraction 95%), glycidyl methacrylate (molar fraction 4%) (Aldrich) and methacryloxypropyltrimethoxy silane (molar fraction 1%) were dissolved, at 20% w/v total concentration, in dried tetrahydrofuran (THF) in a round-bottomed flask, equipped with condenser, magnetic stirring and nitrogen connection. The solution was degassed by alternating a nitrogen purge with a vacuum connection, over a 30 min period. Azoisobutyronitrile (AIBN) (13 mg) which was then warmed to 65° C., and was maintained at this temperature under a slightly positive pressure of nitrogen for 24 hours. After the polymerization was completed, the solution was diluted 1 to 1 with THF and the polymer precipitated by pouring the solution in petroleum ether (ratio THF/petroleum ether 1:10). The polymer was dried under vacuum for 2 h at 80° C.

Example 3: Capillary Coating with copoly(dimethylacrylamide-co-N-acryloyloxysuccinimide-co-methacryloxypropyltrimethoxy Silane)

A capillary, with an internal diameter of 75 μm, was flushed with ethanol for 30 minutes, with 1M NaOH, for 30 minutes, rinsed with water and then treated with 1M NaCl for 1 hour and finally rinsed with water for 3 minutes.

A 1% solution of copoly(dimethylacrylamide-co-N-acryloyloxysuccinimide-co-methacryloxypropyltrimethoxy silane) of example 1 was prepared in ammonium sulphate at 20% of saturation and flushed in the capillary for 20 minutes. The capillary was rinsed with water and dried in a vacuum oven while connected to a stream of nitrogen for 20 minutes.

The residual reactive moieties of the polymer coating were blocked by flushing the capillary for 10 minutes with a solution of 50 mM ethanolamine or with a 1% w/v solution of aminomethoxypolyethylenglycol 2,000 in TRIS/HCl buffer at pH 9 and heated at 50° C. The flow was stopped and the blocking solution was let to sit in the capillary for 15 minutes at 50° C. The capillary was then washed with water and dried with nitrogen.

Example 4: Capillary Coating with copoly(dimethylacrylamide-co-glycidyl methacrylate-co-methacryloxypropyltrimethoxy silane)

A capillary, with an internal diameter of 75 μm, was flushed with ethanol for 30 minutes, with 1M NaOH, for 30 minutes, rinsed with water and then treated with 1M NaCl for 1 hour and finally rinsed with water for 3 minutes.

A 1% solution of copoly(dimethylacrylamide-co-glycidyl methacrylate-co-methacryloxypropyltrimethoxy silane) of example 2 was prepared in ammonium sulphate at 20% of saturation and flushed in the capillary for 20 minutes. The capillary was rinsed with water and dried in a vacuum oven while connected to a stream of nitrogen for 20 minutes.

The residual reactive moieties of the polymer coating were blocked by flushing the capillary for 10 minutes with a solution of 50 mM ethanolamine in TRIS/HCl buffer at pH 9 and heated at 50° C. The flow was stopped and the blocking solution was let to sit in the capillary for 15 minutes at 50° C. The capillary was then washed with water and dried with nitrogen Example 5: Electroosmotic Flow (EOF) Suppression in Capillaries Coated as Reported in Example 4

Figure 1:
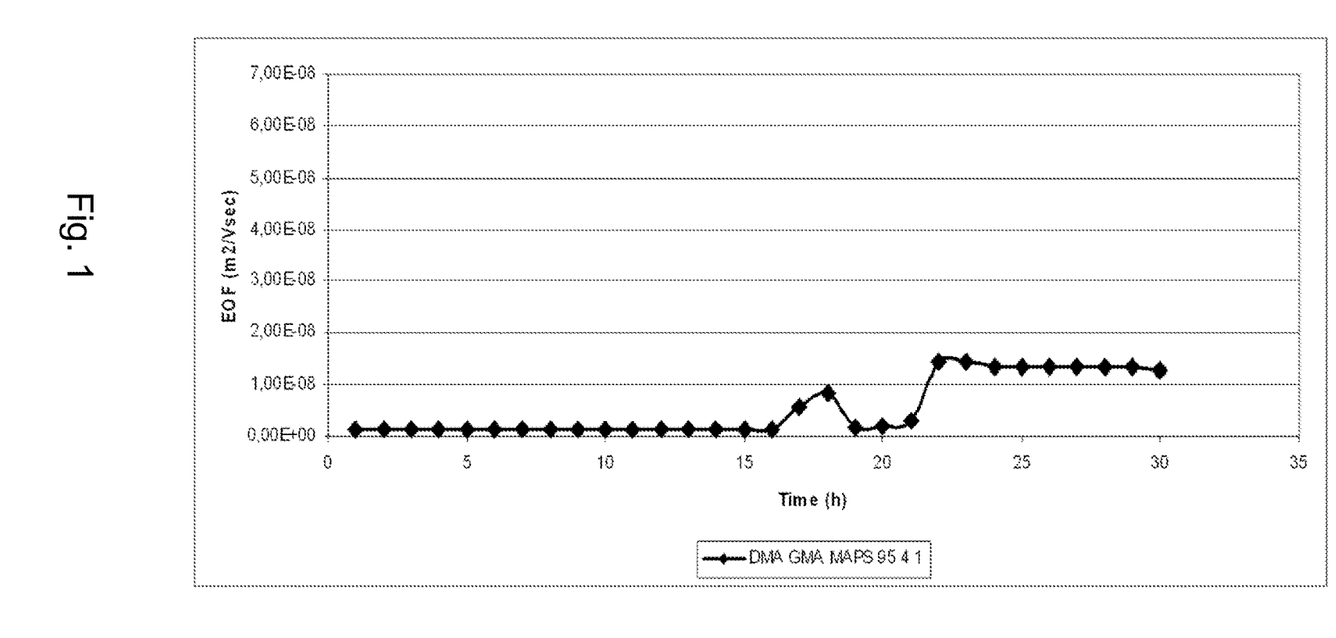
FIG. 1: EOF suppression in an electrophoresis capillary coated with copoly(DMA-GMA-MAPS) blocked as described in example 4. The electrophoretic conditions were: P/ACE™ MDQ Capillary Electrophoresis System, Beckman; running buffer, 25 mM Bicine Tris, pH 8.5; capillary internal diameter, 75 µm, total length 32 cm, length to the window 22 cm; column temperature: 25° C.; detection wavelength: 214 nm; pressure injection 0.3 psi, 2 seconds; applied voltage: 15 kV; neutral marker: acrylamide 0.8% w/V in DI water.

Electroosmotic flow was measured in a capillary coated as reported in example 4 using 25 mM Bicine-TRIS at pH 8.5 as background electrolyte and applying a potential of 15 kV. FIG. 1 shows that the EOF is suppressed for 20 hours of continuous use. During the testing period, an EOF lower than 2×10-9 cm2V/s was measured using the neutral marker injection method (J. W. Jorgenson, K. D. Lukacs, Anal. Chem. 53 (1981) 1298). These results demonstrate that the capillary treated as reported in example 4 has a polymeric layer on its surface of sufficient stability and thickness that reduce EOF to a negligible value.

Example 6: Electroosmotic Flow (EOF) Suppression/Control in Capillaries Coated as Reported in Example 3

Figure 2:
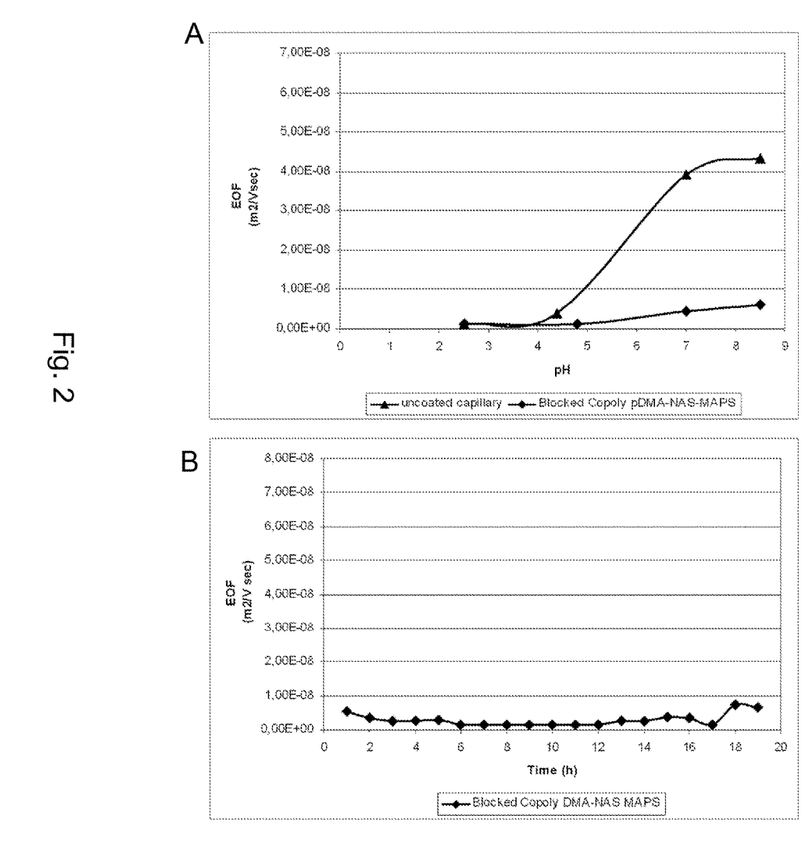
FIG. 2: Dependence of EOF on the running buffer pH (A) and EOF stability over time in 25 mM Bicine/TRIS buffer at pH 8.5 (B) in capillaries coated with copoly(DMA-NAS-MAPS), blocked as described in example 3. Background electrolytes: sodium phosphate, pH 2.5, 6-Aminocaproic Acid (6-EACA)/Acetic Acid pH 4.4, sodium phosphate, pH 7 and Bicine/TRIS, pH 8.5. The other running conditions are as in FIG. 1.

Electroosmotic flow was measured in a capillary coated as reported in example 3 using buffers of different pHs. FIG. 2A shows the EOF dependence on pH: the EOF is negligible below pH=5 and one order of magnitude lower than in an uncoated capillary at pH 8.5.

FIG. 2B shows that the EOF in a capillary coated as reported in example 3 in 25 mM Bicine-TRIS at pH 8.5 is constant over a period of 20 hours of use.

Example 7: Protein Separations in Capillaries Coated as Reported in Example 3

Figure 3:
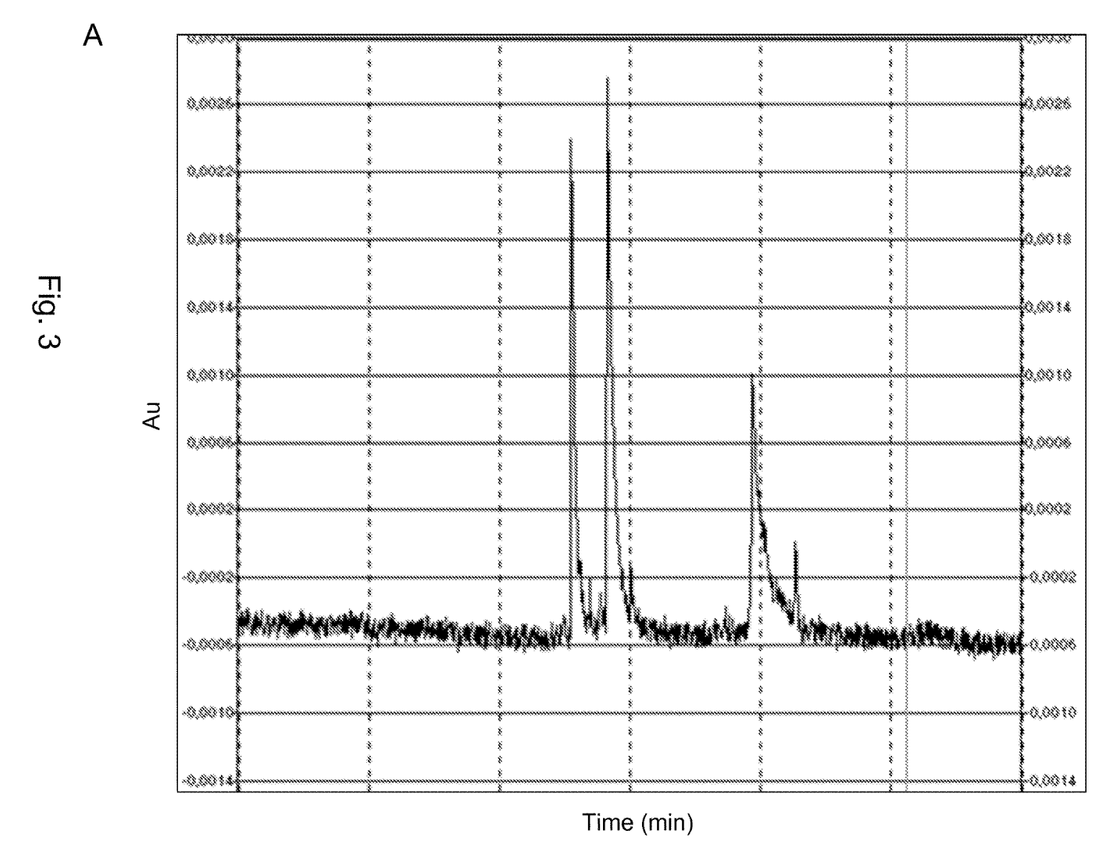
FIG. 3: Separation of lysozime, cytocrome C, ribonuclease A in 25 mM sodium phosphate buffer pH 3.1 in capillaries coated with copoly(DMA-NAS-MAPS) as described in example 3 and blocked with ethanolamine (A) or aminomethoxypolyethyleneglycol 2,000 (B). The separation conditions used were: capillary internal diameter: 30 µm; total length 110 cm; length to the window 100 cm; column temperature: 25° C.; detection wavelength: 214 nm; pressure injection 0.5 psi for 5 seconds; applied voltage 30 kV.

Typical example of protein separation in a capillary coated as reported in example 3 and blocked with ethanolamine (FIG. 3A) and with aminoPEG (FIG. 3B). Separation conditions: running Buffer: 25 mM sodium phospahte pH 3.1; capillary internal diameter: 30 μm; total length 110 cm; length to the window 100 cm; column temperature: 25° C.; detection wavelength: 214 nm; pressure injection 0.5 psi for 5 seconds; applied voltage 30 kV; sample: lysozime, cytocrome C, ribonuclease A.

Example 8: Glass Slides Coating with the Polymers of Example 1 and 2

Coating the glass slides requires two steps:
a) surface pre-treatment and
b) adsorption of the polymer.

In the first step, the slides were washed with 1 M NaOH for 30 min, with 1 M HCl for 30 min, with water and dried. In the second step, pre-treated glass slides were immersed for 30 min in a solution of 1% w/v polymer dissolved in a water solution of ammonium sulphate at 20% of saturation. The slides were then washed extensively with water and dried in a vacuum oven at 80° C. The slides were either blocked or not by an ethanolamine treatment to remove unreacted functional groups. The process is illustrated on FIG. 4.

Figure 4:
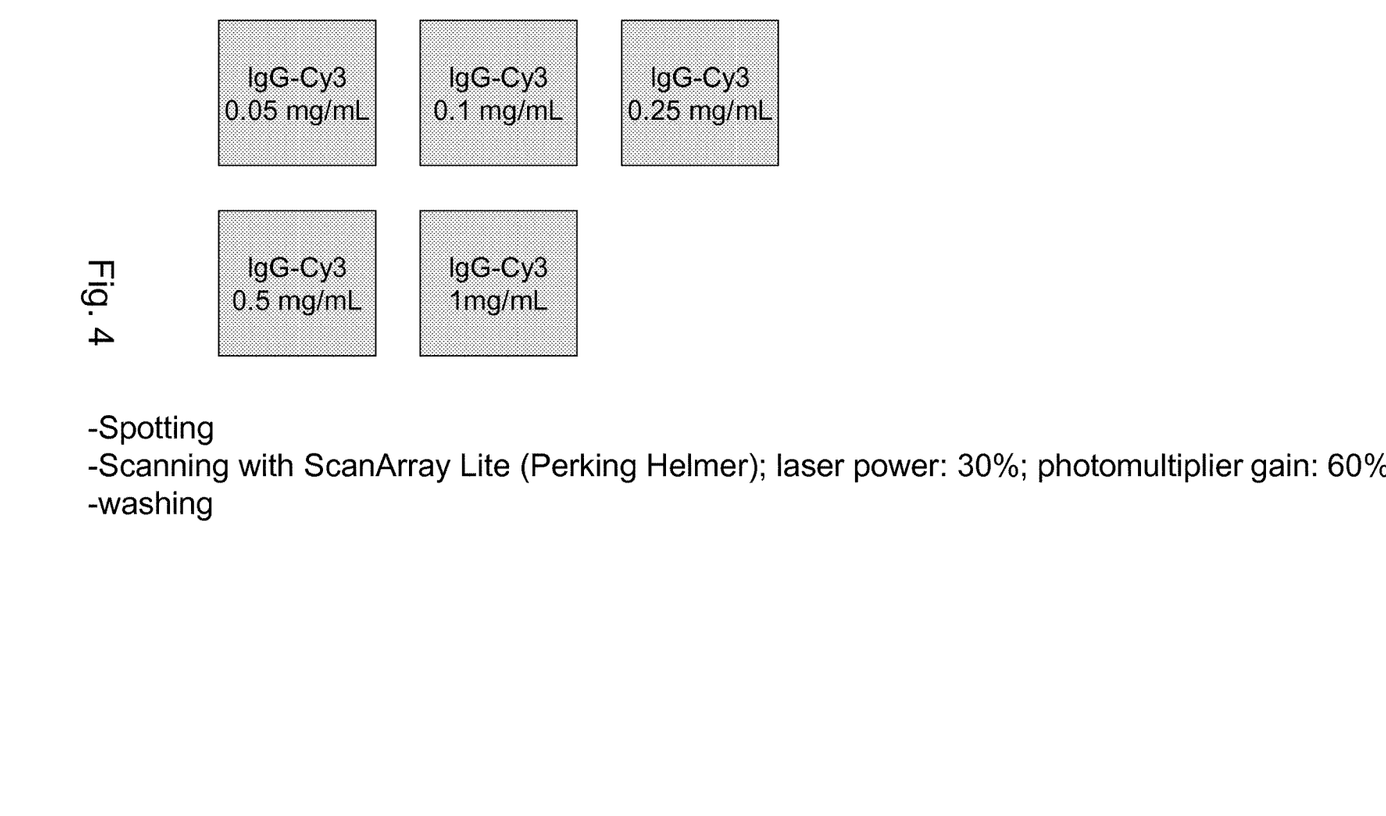
FIG. 4: Adsorption of IgG proteins, fluorescently modified by a Cy3 label. The figure represents the spotting scheme and experimental conditions.
Figure 5:
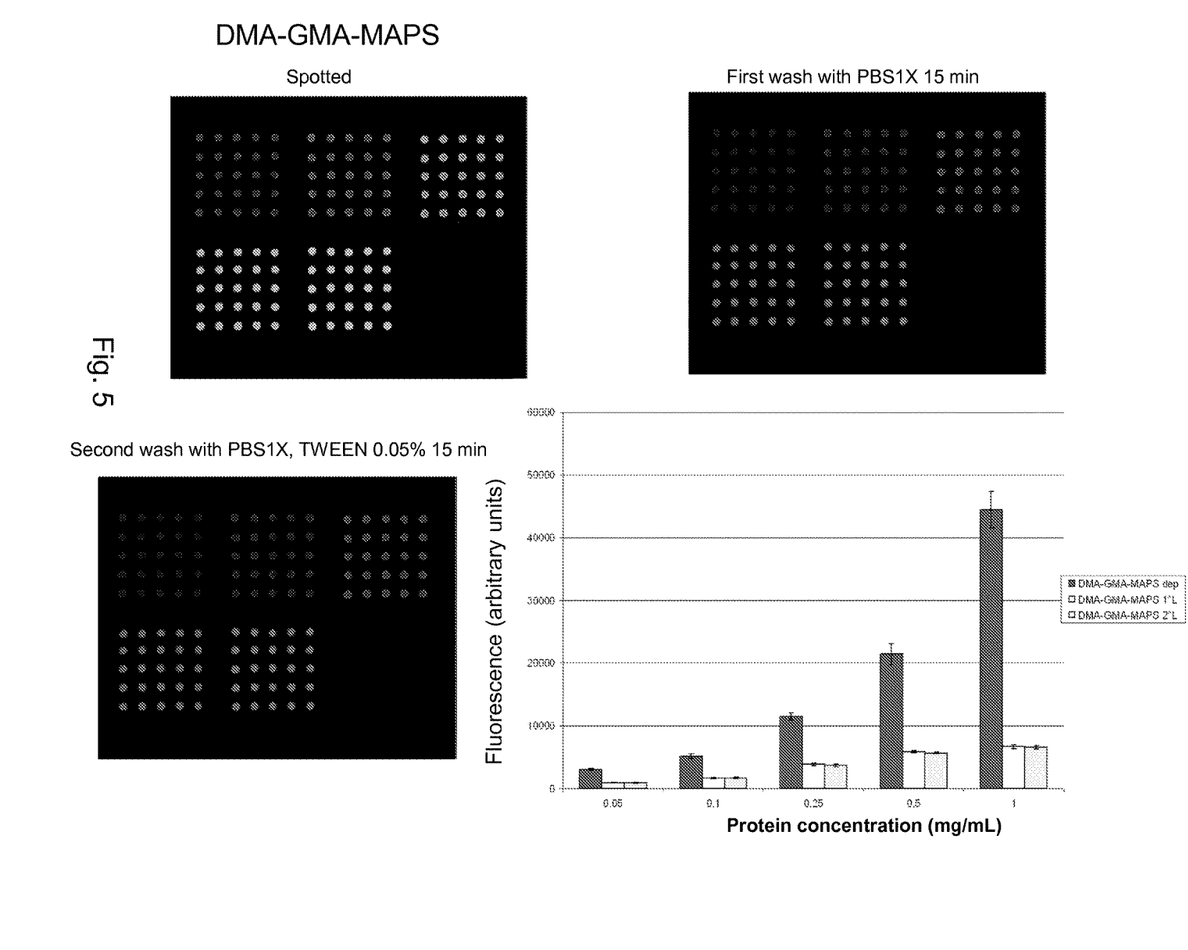
FIG. 5: Glass slide coated with copoly(DMA-GMA-MAPS) spotted with fluorescently labelled IgG proteins and washed with PBS buffer two times. The surface is scanned for fluorescence detection immediately after the spotting and after the washing steps. DMA-GMA-MAPS dep=spotted copoly(DMA-GMA-MAPS), DMA-GMA-MAPS 1° L=copoly(DMA-GMA-MAPS) after first wash, DMA-GMA-MAPS 2° L=copoly(DMA-GMA-MAPS) after second wash.
Figure 6:
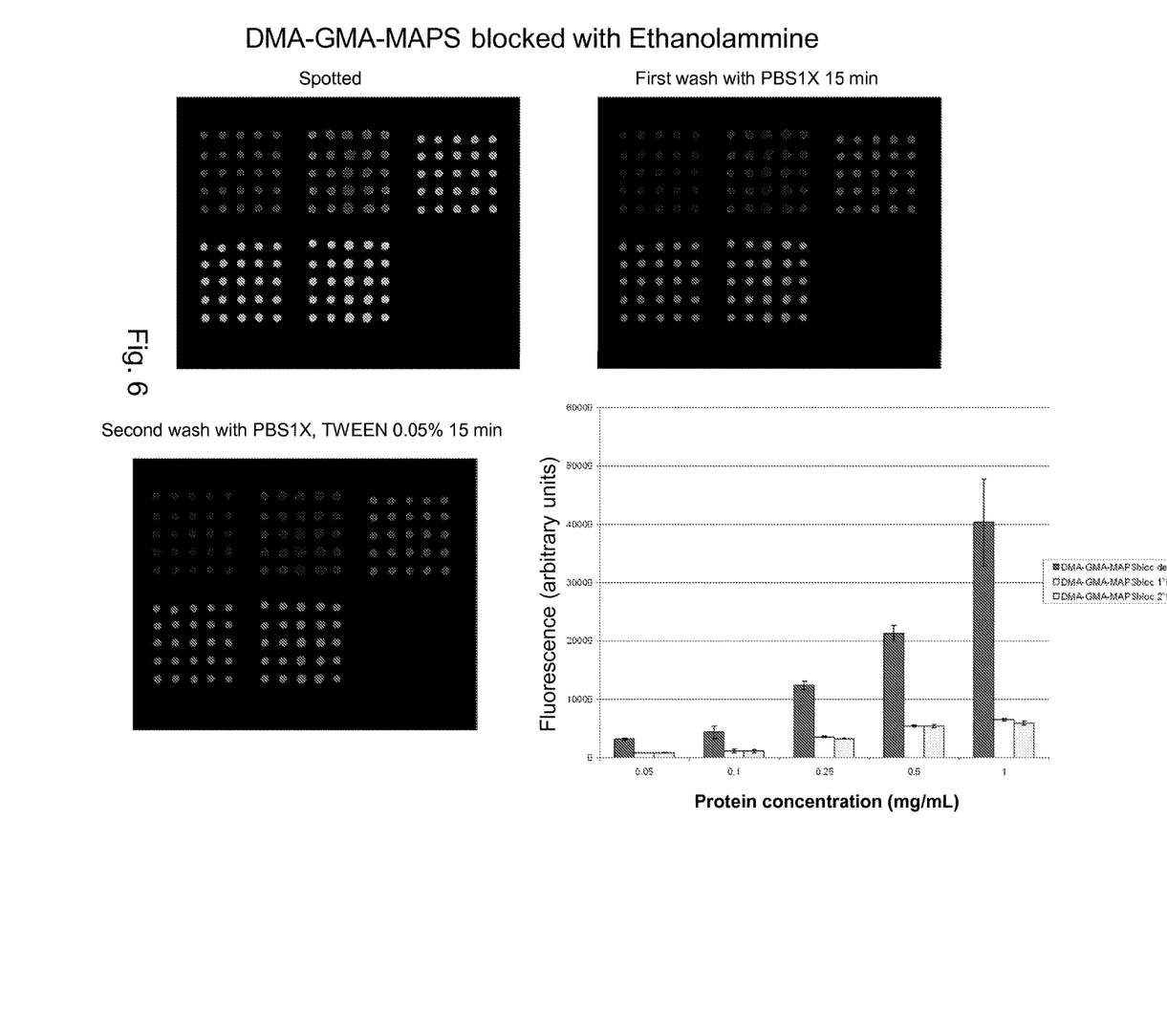
FIG. 6: Glass slide coated with copoly(DMA-GMA-MAPS), blocked with ethanolamine and spotted with fluorescently labelled IgG proteins and washed with PBS buffer two times. The surface is scanned for fluorescence detection immediately after the spotting and after the washing steps. DMA-GMA-MAPSbloc dep=spotted blocked copoly (DMA-GMA-MAPS), DMA-GMA-MAPSbloc 1° L=blocked copoly(DMA-GMA-MAPS) after first wash, DMA-GMA-MAPSbloc 2° L=blocked copoly(DMA-GMA-MAPS) after second wash.
Figure 7:
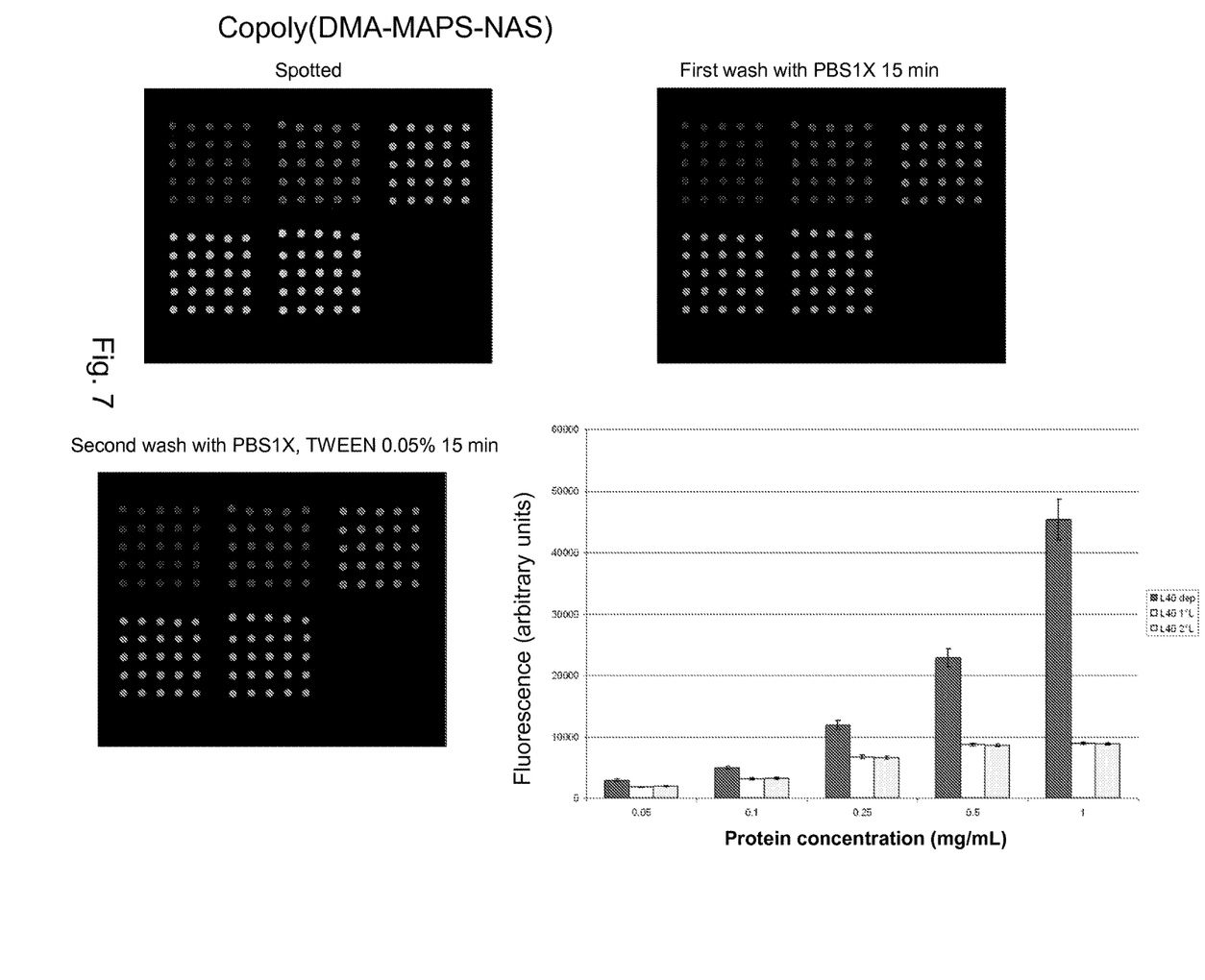
FIG. 7: Glass slide coated with copoly(DMA-NAS-MAPS) spotted with fluorescently labelled IgG proteins and washed with PBS buffer two times. The surface is scanned for fluorescence detection immediately after the spotting and after the washing steps. L40 dep=spotted copoly(DMA-NAS-MAPS), L40 1° L=copoly(DMA-NAS-MAPS) after first wash, L40 2° L=copoly(DMA-NAS-MAPS) after second wash.
Figure 8:
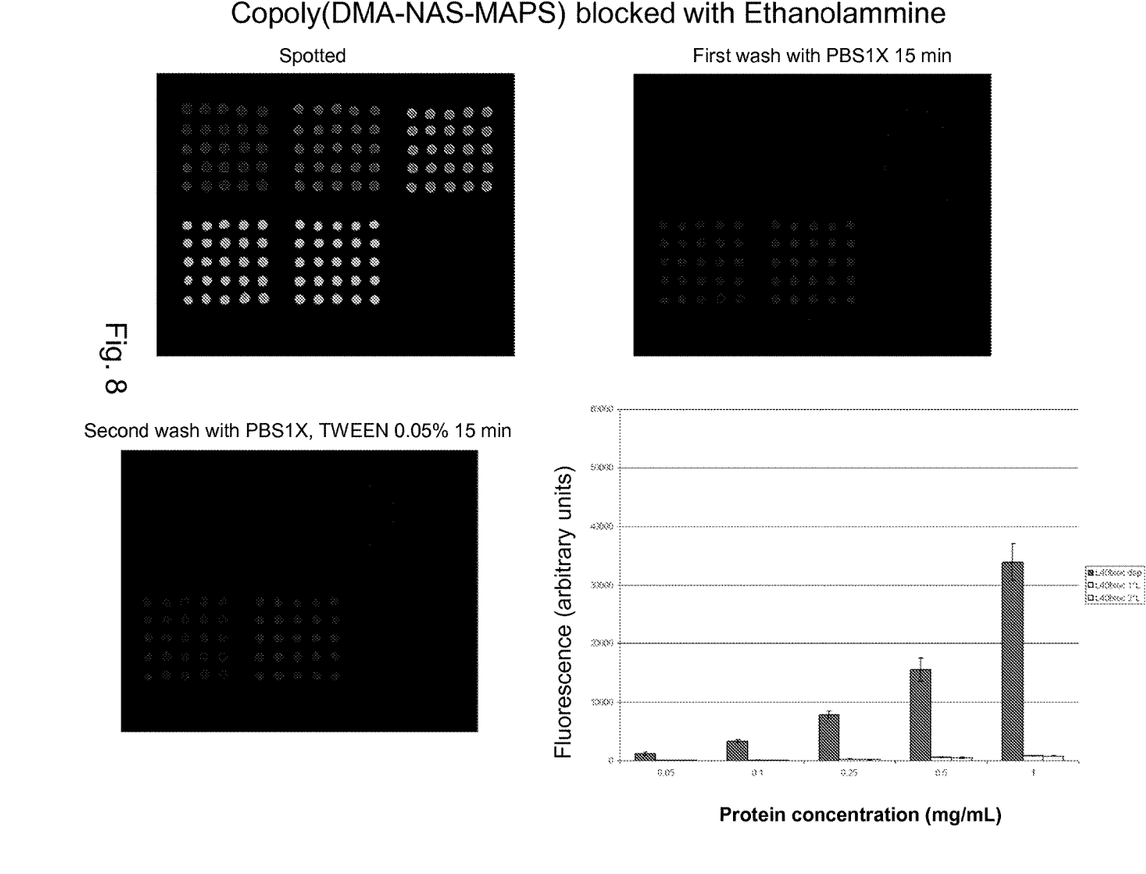
FIG. 8: Glass slide coated with copoly(DMA-NAS-MAPS), blocked with ethanolamine and spotted with fluorescently labelled IgG proteins and washed with PBS buffer two times. The surface is scanned for fluorescence detection immediately after the spotting and after the washing steps. L40bloc dep=spotted blocked copoly(DMA-NAS-MAPS), L40bloc 1° L=blocked copoly(DMA-NAS-MAPS) after first wash, L40bloc 2° L=blocked copoly(DMA-NAS-MAPS) after second wash.

Example 9: Binding of Proteins on Blocked and Unblocked copoly(DMA-GMA-MAPS) and copoly(DMA-NAS-MAPS) Coated Glass Slides Fluorescently labelled Immunoglobulines G were spotted at different concentrations on the surface of a glass slide coated as reported in example 4. After an overnight immobilization step in a humid chamber, the surface was imaged for fluorescence with a scanner and then washed for different amounts of time with different buffers. In FIG. 4, the spotting scheme and the washing steps are depicted along with the scanner settings.

In FIGS. 5-8, the fluorescent images of surfaces coated with the different polymers, blocked or not with ethanolamine are shown. The histograms reported on these figures summarize the average spot intensity measured at the different IgG concentrations. The results clearly show in FIGS. 7 and 8 that the surface coated with the copolymer of the example 1 binds biomolecules with a good efficiency as shown by the fluorescence intensity of the spots after washing the excess of unbound molecules. Only after blocking NAS functionalities with ethanolamine, the coating prevents adsorption or adhesion of proteins (FIG. 8) where almost no fluorescence is detectable after the washing steps. On the contrary, the surface coated with the polymer of example 2 has a lower tendency to bind proteins (FIGS. 5 and 6) even when the epoxy groups are not blocked with ethanolamine, as indicated by the low florescence left on the surface after the washing steps, suggesting that, at low epoxy content, these functionalities, being oriented toward the surface, are not available for binding. Combining the results of examples 5 and 9 it appears that the polymer of example 2 represents an excellent coating for its ability to suppress both EOF and protein adsorption. Both qualities are highly desirable in capillary electrophoretic separations. Instead, the polymer of example 1 forms a coating that, when blocked with ethanolamine, completely suppress protein/surface interaction. Its ability to reduce or suppress EOF in a pH depend manner, makes also this polymer suitable for electrophoretic separations in which the EOF doesn't need to be suppressed but only reduced.

The invention claimed is:

1. A method to reduce the electroosmotic flow in an electrophoresis capillary comprising the steps of:
   providing an electrophoresis capillary with an internal copolymer coating,
   subjecting the internally coated electrophoresis capillary to the electroosmotic flow;
   wherein the copolymer comprises copolymerized dimethacrylamide, glycidal methacrylate and gamma-(meth)-acryloxypropyltrimethoxy silane or wherein the copolymer comprises copolymerized dimethacrylamide, N-acryloyloxysuccinimide and gamma-(meth)-acryloxypropyltrimethoxy silane, and wherein dimethacrylamide is present in an amount of 95% by weight, glycidyl methacrylate is present in an amount of 4% by weight and gamma-(meth)-acryloxypropyltrimethoxy silane is present in an amount of 1% by weight or wherein dimethacrylamide is present in an amount of 97% by weight, N-acryloyloxysuccinimide is present in an amount of 2% by weight and gamma-(meth)-acryloxypropyltrimethoxy silane is present in an amount of 1%.

2. The method of claim 1, in which the copolymer comprises copolymerized dimethylacrylamide, glycidyl methacrylate and gamma-(meth)-acryloxypropyltrimethoxy silane.

3. The method of claim 1, wherein the chemically active group is blocked.

4. The method of claim 1, wherein the capillary or micro-channel or nano-channel is pre-activated by a washing step with NaOH and/or acidic solutions or by plasma treatment.

5. The method of claim 1, wherein the chemically active group is blocked with use of a blocking agent which is ethanolamine, aminomodified polyethylene glycol, peptides, peptoids, or a synthetic polymer.

6. The method of claim 1, wherein the chemically active group is blocked with use of a blocking agent which is ethanolamine, aminomodified polyethylene glycol, or a synthetic polymer.

7. The method of claim 1, wherein the chemically active group is blocked with use of ethanolamine.

8. The method of claim 1, wherein the copolymer comprises copolymerized dimethacrylamide, N-acryloyloxysuccinimide and gama-(meth)-acryloxypropyltrimethoxy silane.

* * * * *